United States Patent [19]
Fages et al.

[11] Patent Number: 5,725,579
[45] Date of Patent: Mar. 10, 1998

[54] PROCESS FOR TREATING BONE TISSUE AND CORRESPONDING IMPLANTABLE BIOMATERIALS

[75] Inventors: Jacques Fages, Portet Sur Garonne; Alain Marty, Toulouse; Didier Combes, Escalquens; Jean-Stéphane Condoret, Toulouse, all of France

[73] Assignee: Bioland, Toulouse, France

[21] Appl. No.: 568,406

[22] Filed: Dec. 6, 1995

Related U.S. Application Data

[63] Continuation of Ser. No. 163,775, Dec. 9, 1993, abandoned.

[30] Foreign Application Priority Data

Dec. 21, 1992 [FR] France .................. 92 15577

[51] Int. Cl.$^6$ .................. A61F 2/28; A61F 2/54
[52] U.S. Cl. .................. 623/16; 623/66
[58] Field of Search .................. 623/16, 11, 66; 435/268; 452/149; 424/49; 62/63

[56] References Cited

U.S. PATENT DOCUMENTS

| | | | |
|---|---|---|---|
| 4,430,760 | 2/1984 | Smestad | 623/16 |
| 4,678,470 | 7/1987 | Nashef et al. | 623/16 |
| 4,749,522 | 6/1988 | Kamarei | 260/412.8 |
| 4,776,173 | 10/1988 | Kamarei et al. | 62/63 |
| 4,789,663 | 12/1988 | Wallace et al. | 623/16 |
| 4,932,923 | 6/1990 | Gendler | 623/16 |
| 4,946,792 | 8/1990 | O'Leary | 623/16 |
| 5,053,049 | 10/1991 | Campbell | 623/16 |
| 5,112,354 | 5/1992 | Sines | 623/16 |
| 5,122,365 | 6/1992 | Murayama | 424/49 |
| 5,162,016 | 11/1992 | Malloy | 412/149 |

FOREIGN PATENT DOCUMENTS

| | | |
|---|---|---|
| 0 603 920 A1 | 6/1994 | European Pat. Off. . |
| 603920 | 6/1994 | European Pat. Off. . |
| 2175506 | 12/1986 | France . |
| 2695140 | 3/1994 | France . |
| 8703812 | 7/1987 | WIPO . |
| 9107194 | 5/1991 | WIPO . |
| WO 93/17724 | 9/1993 | WIPO . |
| 9403590 | 2/1994 | WIPO . |

*Primary Examiner*—Debra S. Brittingham
*Attorney, Agent, or Firm*—Shlesinger Arkwright & Garvey LLP

[57] ABSTRACT

The present invention concerns a process for treating bone tissue of animal or human origin, and a corresponding implantable biomaterial. According to the present invention, a fluid in the supercritical state is caused to penetrate throughout the bone tissue. The bone tissue thus treated can then undergo stages of extracting specific proteins. This tissue is intended to be placed on a damaged bone tissue and has mechanical properties at least equivalent to those of natural bone.

21 Claims, 1 Drawing Sheet

PROCESS FOR TREATING BONE TISSUE AND CORRESPONDING IMPLANTABLE BIOMATERIALS

This application is a continuation of application Ser. No. 08/163,775, filed Dec. 9, 1993, now abandoned.

The present invention relates to a process for treating bone tissue and corresponding implantable biomaterials.

In particular such a process enables bone tissue to be treated with a view to its being implanted into a human. Such a tissue must not cause rejection (or at least as little as possible), and must have a good osteoconductive capacity, ie it must allow the formation and migration of bone tissue which has been newly formed by the recipient.

The grafting of bone tissue is a technique used daily in most orthopaedic surgery departments throughout the world. These grafts may be of three types, namely:

allografts,
autografts,
xenografts.

Bone allografts consist in implanting bone tissue from a donor into a recipient of the same species, but different from the donor. Bone autografts consist of removing bone tissue and grafting it into the same individual. Bone xenografts consist of implanting bone tissue from an animal (often a pig or a bovine) into a human individual.

To carry out these grafts, the starting point is bone tissue which is treated to clean it mechanically and purify it of all materials which would adversely affect its implantation. In doing this, it is found, with the treatments used in the prior art, that the mechanical properties of the bone tissue are impaired. This is because the organic substances extracted influence the mechanical properties of the bone. However, the grafting of a bone implant is generally carried out for the purpose of restructuring the skeleton, in a part which is subject to problems of strength in which the mechanical properties are of the utmost importance. It would therefore be advantageous to have available bone grafts with mechanical properties which are equivalent, or even superior, to those of natural bone.

For example such grafts would be indicated in orthopaedic applications and in particular when the graft is put under load, ie in particular: spinal surgery (cervical fusion, replacement of lumbar discs, etc), reconstruction of the base of the cotyle, arthroplastic surgery, osteotomy, pseudoarthrosis, arthrodesis, etc.

Thus, when the graft is used to restore a part of the skeleton which supports an implanted artificial prosthesis (joint prosthesis, dental prosthesis, etc), the use of a graft whose mechanical strength, particularly under compression, would be greater than that of the original deteriorated bone, would be a decisive advantage from the point of view of the life and functioning of the prosthesis. Furthermore, the graft inserted between the prosthesis and the natural bone would make the variations in mechanical properties more gradual and would improve the quality of the transmission of stresses by avoiding excessively steep localised gradients in strength. Furthermore, if the graft has, from the time it is implanted, strengths equivalent to those of the bone, all risk of deterioration during the resorption of the graft by a newly formed bone tissue is eliminated.

The aim of the invention is therefore to propose an implantable biomaterial whose mechanical properties, particularly strength under compression, are at least equivalent to those of natural bone. In particular, the invention aims to propose an implantable biomaterial whose strength under compression can be between one and two times that of natural bone.

Furthermore, the invention also aims to propose a biomaterial which improves the efficacy of bone grafts both from the mechanical and from the biological point of view.

Indeed, allografts have numerous drawbacks. First of all the risks of infection related to the transmission of bone tissue from one individual to another are many. Such is the case in particular where the transmission of the AIDS HIV virus is concerned. Given the large increase in this illness, such a risk of infection has increased considerably in recent years. Apart from these risks of infection, which also concern other viruses, the main complications related to the use of allografts are fractures, an unsuccessful recolonisation of the implanted bone tissue (grafts) and rejection of the implant. The unsuccessful recolonisation of the grafts today poses a significant problem. This is because the tissues of the graft are supposed to be resorbed, invaded and then replaced by newly-formed bone tissue. But until now this rehabilitation has been somewhat weak.

One of the aims of the present invention is therefore to produce an implantable bone tissue which is safe from the point of view of infection and the immune system.

Another aim of the invention is that a bone tissue of this kind should have a good osteoconductive capability (ie one that facilitates a successful recolonisation of the grafts).

Autografts are often preferred to allografts because they are more successfully recolonised and likely to contribute bone cells at the site of a graft. The result of this is that the risks of infection and to the immune system are considerably reduced, but this type of practice is not completely satisfactory. This is because it is painful, often meets with an unfavourable response from the patient, and involves a risk of complications at the donor site. In addition, numerous operations require large quantities of bone tissue, which is incompatible with autografts.

Bone xenografts also have many drawbacks. Generally, these grafts cause strong immune reactions (rejections). To mitigate this drawback, various attempts aiming to reduce or eliminate these reactions have been made. They are generally based on the principle of extracting the protein from the bone tissue before implantation. This is because the proteins contained in the bone tissue are the cause of some of the rejection reactions. These rejection reactions are also related to the presence of cell debris in the medullary tissue and to other elements of this tissue.

The use of organic solvents for extracting proteins from bone tissue is known. The most commonly used solvents are: ethylene diamine, hydrogen peroxide, various chlorinated solvents such as chloroform or dichloromethane, and also ethanol and acetone. With the protein thus extracted most bone tissues present little or no immune reaction. They are generally revascularised successfully and are invaded by osteogenic cells from the recipient. However, they do not themselves have osteoinductive properties. Their mechanical strength is generally lower than or similar to that of natural bone.

It will however be noted that the solvents used for protein extraction are often highly toxic. Because of this, the bone tissues have to be carefully rinsed (which is not easy, given their porosity) to avoid any pollution of the recipient site.

The patent FR-A-2.654.625 describes a protein extraction process using such toxic solvents combined with a selective urea-based extraction agent. However, such a process results in very variable extraction of lipids, because according to this patent 0.5 to 5% of lipids may remain.

Fluids in the supercritical state are already known for extracting various substances such as lipids, proteins, nucleotides, and saccharides from animal tissues or organs.

However, these known processes are considered to be complex and costly to use, without having any decisive advantages compared with other extraction processes.

Thus the prior art does not disclose the possibility of extracting organic matter when treating bone tissue as a result of which extraction the mechanical strength of the bone tissue is improved.

The aim of the present invention is to mitigate all the drawbacks of the prior art and in particular to propose an implantable bone tissue with improved strength compared with that of natural bone, which is safe with respect to infection and the immune system, which has a good osteoconductive capability and which does not use toxic products. The present invention has the particular aim of proposing a process enabling such bone tissue to be treated.

For this purpose, the present invention concerns a process for treating animal or human bone tissue in order to obtain biomaterial which can be implanted in a human and is suitable for sustaining mechanical stresses, in which the bone tissue is mechanically cleaned of all the organic matter surrounding it and the organic matter is extracted from the bone tissue, characterised in that it includes at least one stage in which a fluid in the supercritical state is caused to penetrate throughout the bone tissue.

The inventors thus found, to their surprise, that it is enough simply to bring the bone tissue into contact with a supercritical fluid in the course of the treatment in order to increase its mechanical strength at the same time as the organic materials are extracted.

According to the invention, the fluid in the supercritical state is made to penetrate the bone tissue in a stage in which the essentially lipidic organic matter present in the tissue, and which is solubilised in the fluid in the supercritical state, is extracted. The extraction thus effected by this supercritical fluid has properties which are particularly suitable for bone tissue.

According to the invention, the process consists of:

a) cleaning the bone tissue mechanically of all the organic matter surrounding it, b) cutting this bone tissue according to a predetermined shape, c) cleaning the bone tissue in order to extract therefrom constituents harmful to a successful reimplantation, causing to penetrate throughout the bone tissue a fluid in the supercritical state suitable for solubilising and extracting the essentially lipidic organic matter present in this tissue, d) washing, dehydrating and sterilising the bone tissue that has been cleaned in this way. The cleaning stage c) consists in addition of treating the bone tissue chemically and/or enzymatically in order to extract therefrom specific proteins remaining therein.

The fluid in the supercritical state, ie one having low dynamic viscosity (close to that of a gas), a high diffusion coefficient, very low interfacial surface tension and high density (close to that of a liquid) diffuses easily through the porous material without any absorptivity problem. In addition, the solvent power of such a fluid is high (close to that of liquids and sometimes up to $10^8$ times that of a gas), and may be modified by varying the pressure. The result of this is that such a fluid in the supercritical state dissolves the essentially lipidic organic matter present in the bone tissue easily and virtually completely. The risks to the immune system and of infection are thereby considerably reduced.

One of the advantages of the invention lies in the use of carbon dioxide ($CO_2$) as a fluid in the supercritical state, because this constituent has many advantageous properties, ie:

its critical temperature, 31° C., is low. It is thus possible to have carbon dioxide in the supercritical state while working at a temperature of around 31° and a pressure of around 7.38 MPa. According to the pressure applied, it is possible to work at temperatures between 31° and 60° C., at which temperatures the only possible form of impairment of the bone tissue is a denaturing of the collagen which takes away its antigenic character, its solvent power is excellent, in particular for lipids. For example, it is known that many fatty acids and triglycerides may have solubilities in carbon dioxide in the supercritical state of up to 10%. However, these lipids are present in large quantities in the medullary tissues which impregnate spongy bone tissue, they are strongly antigenic and always very difficult to eliminate; in addition, since they are not absorptive, they form a physical barrier preventing the recolonisation of the graft, it reinforces the biomechanical properties of the bone and assists the osteointegration of the implanted bone tissue, it is a natural, entirely non-toxic, substance, it is easy to obtain and presents no danger either for the substance treated or for the experimenter.

Advantageously the treatment of the bone tissue is supplemented by a chemical or enzyme treatment which is particularly suitable for extracting the protein materials present in bone tissue.

The present invention also concerns an implantable biomaterial obtained according to the process indicated above, and consisting of a purified bone tissue which has been brought into contact with a fluid in the supercritical state, the said tissue being suitable for being implanted into a human at a site where there is damaged bone tissue.

According to the invention, the bone tissue has been cleansed of the essentially lipidic organic matter by extraction using fluid in the supercritical state.

Such a material has a strength which is equivalent to or greater than that of natural bone, is safe from the point of view of infection and the immune system, is non-toxic and, because of the almost complete extraction of the lipids which it originally contained, has a good osteoconductive capability.

Other objects, characteristics and advantages of the present invention will become clear from the following description, provided by way of non-limiting example, which refers to the accompanying diagram representing an installation for the implementation of the process according to the invention.

Figure 1:
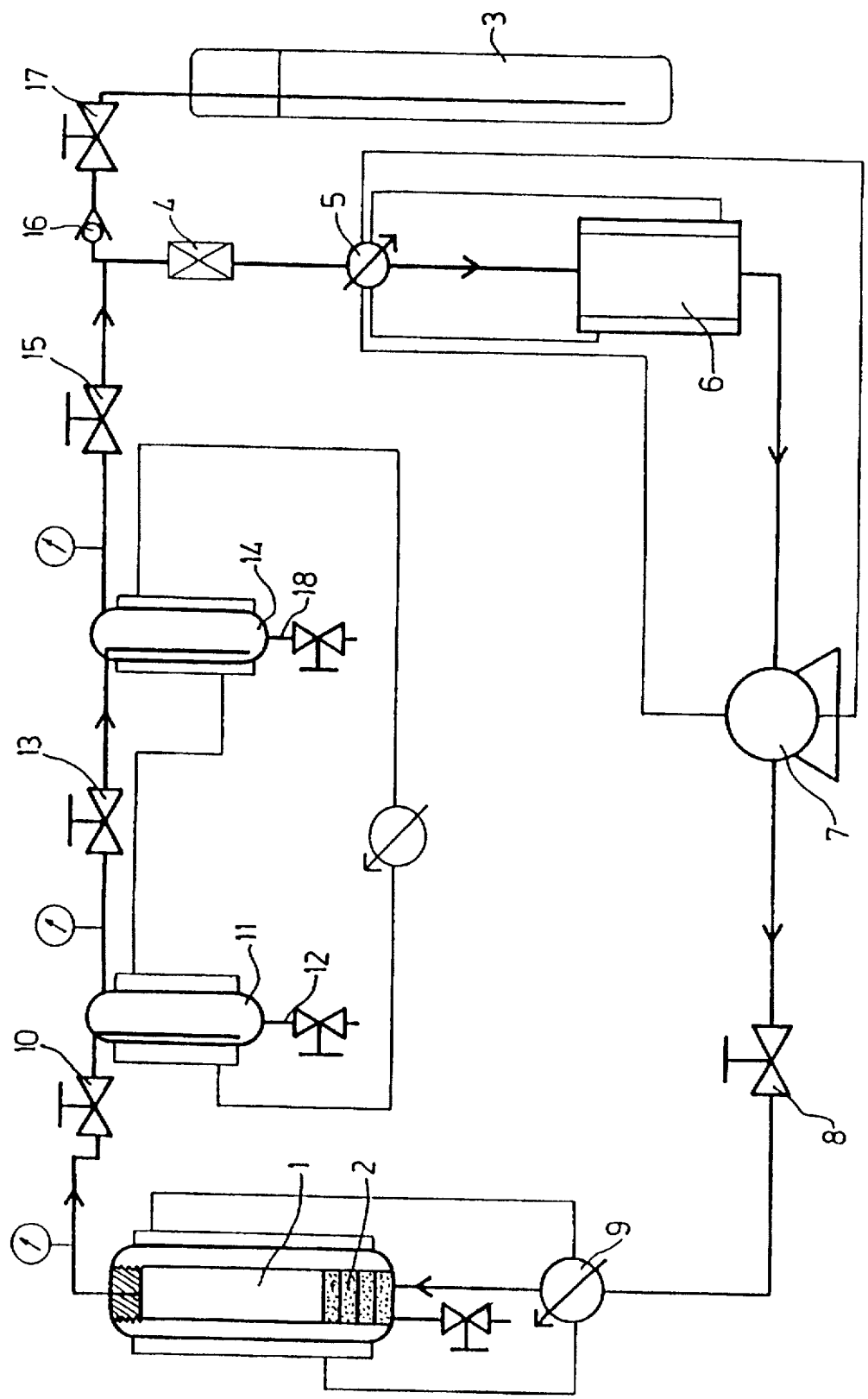
FIG. 1 illustrates an installation for implementation of the process according to the present invention.

The installation shown in the FIG. 1 includes a reactor 1 in which the bone tissue 2 is placed and through which a stream of carbon dioxide $CO_2$ in the supercritical state is passed.

The carbon dioxide is stored in the liquid state in a cylinder 3, passes through a filter 4, is cooled by a refrigerating unit 5 to a temperature, at which it is definitely liquid, of around 0° C., and then fed into a buffer tank 6. A metering pump 7 is placed downstream of the tank 6 to compress the liquid carbon dioxide to a pressure enabling it to change to the supercritical state. A valve 8 is placed downstream of the pump 7 to isolate the reactor 1 for the purpose of charging or discharging it. Before being fed into the reactor 1, the carbon dioxide is heated by a heater 9 so that, on leaving this heater 9, the carbon dioxide is in the supercritical state. The carbon dioxide passes through the reactor 1 and leaves it at the opposite end from the one through which it entered. A valve 10 is placed downstream of the reactor 1 to enable it to be isolated from the circuit. The valve 10 also enables the pressure to be reduced before the carbon dioxide is fed into a first separator 11. The matter dissolved in the carbon dioxide is recovered at the outlet 12 of the separator 11. The installation also comprises a second separation stage comprising a valve 13 causing a further reduction in pressure and a second separator 14 having an outlet 18 for the recovery of the organic matter. More than two separation stages can be provided, as required. The carbon dioxide, at the outlet 12, 18 of the separation stages, is fed back into the circuit by means of a valve 15. The cylinder 3 is connected to this closed circuit by means of a non-return valve 16 and a valve 17.

The treatment process for bone tissue according to the invention is described below.

As is conventional, the bone is first cleaned mechanically, then cut to the desired dimensions and to a predetermined shape. The shape of the bone tissue may for example be a right-angled parallelepiped, a cylinder or any other suitable shape. This bone tissue is then placed in the extraction reactor 1. Optimum operating conditions are achieved at a temperature of between 31° and 60° C. and a pressure of about $1.5 \times 10^7$ to $4 \times 10^7$ Pa.

The carbon dioxide $CO_2$ is pumped in liquid form by the metering pump 7. This liquid is preheated upstream of the extraction reactor 1 in order to be fed into the latter in the supercritical state.

It will be recalled that fluids in the supercritical state may be defined as gases under conditions of temperature and pressure such that their properties are between those of gases and those of liquids. They are also known as "dense gases" or "expanded liquids". For a given chemical substance, the precise point of the temperature pressure diagram at which the two phases, liquid and vapour, come to form only a single phase is known as the critical point. Beyond this critical temperature ($T_c$) and critical pressure ($P_c$), the fluid is in the so-called "supercritical" state.

Passing through the reactor 1, the carbon dioxide in the supercritical state solubilises a large proportion of the organic, essentially lipidic, matter in the bone. In particular, it dissolves the fats in the medullary tissues contained in the bone tissue.

Because of the properties of supercritical fluids, this extraction is highly efficacious. In particular, the fats which are normally inaccessible to the chemical solvents used in the known processes are extracted by the carbon dioxide in the supercritical state.

In order to control the lipidic extraction carried out by the carbon dioxide, the separators 11 and 14 are constantly emptied of the extract, recovering the fatty residues. The bone tissue is left in contact with the supercritical carbon dioxide while a flow of fatty residue is recovered at the outlet 12, 18 of the separators 11, 14. The duration of the treatment varies proportionately to the weight of the bone tissue to be treated and the flow of supercritical carbon dioxide fed into the reactor 1. The process can thus be interrupted by controlling the mass of carbon dioxide passing through the bone tissue, the mass of which is itself determined. Indeed it is known that the mass yield of the extraction is a constant. Thus, using a mass flow meter installed in series with the outlet of the reactor 1, the process can be interrupted when the mass of carbon dioxide used is adequate.

It will be noted that the substances extracted are composed of more than 98% fat. The bone tissue itself contains less than 2% fat on average after treatment, and this amount is evenly distributed. Moreover, its compressive strength is about 10 to 20 MPa.

It will be noted, in contrast to what happens conventionally in a chemical reactor, that it is not the extract (essentially lipidic matter) which is used subsequently, but the residue (the bone tissue).

Thus the fluid in the supercritical state also has the double function of strengthening the bone matter, which improves its biomechanical properties, and of cleansing the bone matter.

The bone tissue which has been treated in this way is subjected to an additional conventional process involving chemical or enzyme treatment to extract specific proteins. The additional chemical treatment may be carried out using hydrogen peroxide, while the enzyme treatment may be effected by means of protease. This additional treatment ensures more effective extraction of the proteins from the bone tissue and decreases accordingly the risk of rejection of the bone tissue which has been treated in this way.

Subsequently, the bone tissue is subjected to a washing process. This washing is carried out in several successive baths of distilled water at a temperature of between 30° and 60° C.

A stage consisting of the dehydration and disinfection of the bone tissue is then carried out. This stage is carried out by passing it through several successive baths of increasingly concentrated ethanol, for example 70%, 95% and 100%. It will be noted that, because ethanol is an excellent virucidin, it makes it possible simultaneously to dehydrate the tissue and increase the safety of the biomaterial with regard to infection. Drying in a ventilated oven at a temperature of between 30° and 60° C. completes this process.

After being packaged, the bone tissue is then subjected to sterilisation. This sterilisation may be carried out by irradiation, either by beta particles or by gamma rays (25 k Gray). It is possible for the bone tissue to be cut again before implantation in order to adapt it to the recipient bone tissue. This is because the bone tissue thus treated is relatively hard and may be cut again without being caused to crumble.

In the following table, the results of analyses of non-treated bone tissue can be seen (Example 1), of bone tissue treated using only $CO_2$ in the supercritical state (Example 2), and of bone tissues treated with $CO_2$ which have undergone an additional stage, either chemical (Example 3) or enzymatic (Example 4).

The respective values for the proportions of organic matter OM, organic carbon C, nitrogen N and lipidic residue (lipids) and the compressive strength are given for each of these four examples. The values given are average values; the tolerance range is given between brackets.

The bone tissues analysed come from the distal ends of a bovine femur.

|  | Example 1: untreated bone | Example 2: bone treated with $CO_2$ | Example 3: bone treated with $CO_2$ + hydrogen peroxide $H_2O_2$ | Example 4: bone treated with $CO_2$ + protease |
|---|---|---|---|---|
| OM (%) | 62.7 | 23.0 | 20.8 | 20.6 |
|  | (50.0–70.3) | (21.6–25.7) | (18.9–21.9) | (16.1–23.6) |
| C (%) | 44.8 | 10.8 | 9.2 | 9.8 |
|  | (43.1–46.5) | (10.1–12.4) | (8.7–10.3) | (8.8–11.6) |

-continued

|  | Example 1: untreated bone | Example 2: bone treated with $CO_2$ | Example 3: bone treated with $CO_2$ + hydrogen peroxide $H_2O_2$ | Example 4: bone treated with $CO_2$ + protease |
|---|---|---|---|---|
| N (%) | 2.4 | 4.1 | 3.9 | 4.0 |
|  | (2.2–2.6) | (3.9–4.3) | (3.3–4.3) | (3.0–4.7) |
| lipids (%) | 51.3 | 1.9 | 1.5 | 1.7 |
|  | (24.7–77.3) | (0.6–5.3) | (0.8–3.0) | (0.8–2.8) |
| Compressive strength | 8.9 MPa | 16.9 MPa | 10.7 MPa | 11.5 MPa |

A second series of identical tests was carried out using bovine bones of a different origin. In the following table, the results are given as an average of 38 measurements for Examples 1 and 4, 39 measurements for Example 2, and 28 measurements for Example 3.

|  | Example 1 | Example 2 | Example 3 | Example 4 |
|---|---|---|---|---|
| OM (%) | 62.1 | 22.8 | 19.6 | 20.6 |
| C (%) | 46.6 | 10.8 | 8.6 | 9.6 |
| N (%) | 2.4 | 4.1 | 3.6 | 4.1 |
| lipids (%) | 51.0 | 1.1 | 0.7 | 1.3 |
| Compressive strength | 10.42 MPa | 14.91 MPa | 10.65 MPa | 11.54 MPa |

With respect to treatment with a fluid in the supercritical state alone (Example 2), a reduction in the carbon and nitrogen content and more generally in organic matter can be noted from Examples 3 and 4. This reduction corresponds to the elimination of the non-lipid fraction of the medullary tissues as well as to the solubilisation of the soluble proteins in the bone tissue. This operation enables inflammatory reactions to be reduced considerably and improves osteoconduction further, as experiments carried out on animals have shown.

It will be noted that the biomechanical properties of these implants are statistically superior to those of the bone from which they are made (Example 1). In fact the compressive strength of the treated bone tissue is superior to that of the untreated control bone tissue.

It will be noted, as a variant of the process described above, that the stages of cleaning and cutting the bone tissue may be carried out in the following manner.

The cleaning stage may be carried out using a blasting process in which corundum (alumina) is applied to the bone at a pressure of between $4.10^5$ and $10^6$ Pa in order to free it of all soft tissue adhering to it, including the periosteum. This technique is much faster and more efficacious than conventional methods, which are all manual, whereas the sanding may be carried out in entirely automatic robotic machines.

The cutting stage may, on the other hand, be water-jet cutting. Such cutting allows accuracy of up to 10 μm, it is carried using a jet of pure water, thus avoiding any risk of contamination from a cutting tool, and it can be used for mass production purposes.

Of course, the present invention is not limited to the chosen embodiment and includes any variant within the competence of a person skilled in the art. Thus the chemical cleaning stage carried out by means of a fluid in the supercritical state may be supplemented by the addition of a fluid dissolved in the fluid in the supercritical state, and the specific action of which on the bone tissue may take place in the reactor itself.

It is then possible to carry out all the protein extraction and delipidation reactions in the same place (the reactor) and at the same time. In addition, the fluid thus dissolved in the fluid in the supercritical state is at a temperature and pressure highly favourable for this type of reaction.

Thus, if it is desired to eliminate proteins from the medullary tissues or from the extracellular bone matrix, or again from the cellular debris of medullary origin, the strong antigen effect of which is largely responsible for immune responses, the following can advantageously be introduced into the reactor circuit: detergents, oxidants for organic matter, enzymes specific to one of other of the reactions and more generally any substance suitable for the desired treatment provided that it is solubilised by $CO_2$ in the supercritical state.

It will be noted that the process and biomaterial described above can be carried out and produced using human or animal bones. They can be used for carrying out a graft, in particular in orthopaedic applications, and in applications in which the graft is subject to mechanical stresses, for example surgery on the spine (cervical fusion, replacement of lumbar discs, etc), reconstruction of the base of the cotyle, arthroplastic surgery, osteotomy, pseudoarthrosis, arthrodesis, etc.

We claim:

1. A process for treating bone tissue to obtain implantable bone grafting tissue with improved mechanical strength, comprising the steps of:
   a) obtaining bone tissue;
   b) removing any organic matter present about said bone tissue; and
   c) treating said bone tissue with a fluid in supercritical state adapted to obtain a tissue containing less than 2% fat on average, said fluid penetrating throughout said bone tissue.

2. The process of claim 1, and including the step of:
   d) cutting said bone tissue to a predetermined shape prior to said fluid treatment step c).

3. The process of claim 2, wherein:
   said cutting step d) is carried out by using a high-pressure water-jet.

4. The process of claim 1, and including the step of:
   e) extracting protein material from said bone tissue.

5. The process of claim 4, wherein:
   said protein extraction step e) comprises treating said bone tissue with hydrogen peroxide.

6. The process of claim 4 wherein:
   said protein extraction step e) comprises treating said bone tissue with an enzyme.

7. The process of claim 6, wherein:
   said enzyme comprises protease.

8. The process of claim 4, and including the step of:
   f) washing the bone tissue obtained in said protein extraction step e) with distilled water at a temperature of about 30° to 60° C.

9. The process of claim 8, and including the step of:
   g) dehydrating the bone tissue obtained in said washing step f) by subjecting the bone tissue to a dehydrating agent.

10. The process of claim 9, wherein:
    said dehydration step g) comprises passing the bone tissue through a bath including about 70% ethanol.

11. The process of claim 9, wherein:
    said dehydration step g) comprises passing the bone tissue through a plurality of successive baths including increasingly concentrated ethanol.

12. The process of claim 11, wherein:

the concentration of ethanol ranges from about 70% to 95%.

13. The process of claim 9, and including the step of:

h) drying the bone tissue obtained in said dehydration step g) in an oven at a temperature of about 30° to 60° C.

14. The process of claim 13, and including the step of:

i) sterilizing the bone tissue obtained in said drying step h) by irradiation.

15. The process of claim 14, and including the step of:

j) packaging the bone tissue obtained in said drying step h) prior to said irrigation step i).

16. The process of claim 1, wherein:

said fluid treatment step c) comprises extracting by solubilizing in said supercritical fluid the lipidic organic matter present in said bone tissue.

17. The process of claim 1, wherein:

said supercritical fluid comprises carbon dioxide.

18. The process of claim 1, wherein:

said fluid treatment step c) is carried out at a temperature of about 30° to 60° C. and a pressure of about $1.5 \times 10^7$ to $4 \times 10^7$ Pa.

19. The process of claim 1, wherein:

said organic matter removal step b) comprises cleaning said bone tissue by blasting with alumina.

20. A bone tissue made in accordance with the process of claim 1.

21. A process for treating bone tissue to obtain implantable bone graphing tissue having improved mechanical strength, comprising the steps of:

a) obtaining bone tissue;

b) removing any organic matter present about the bone tissue; and c) treating the bone tissue with a fluid in supercritical state, the fluid penetrating throughout the bone tissue and with a duration of treatment and flow of fluid adapted to obtain a tissue containing less than 2% fat on average.

* * * * *